United States Patent

Chaney

Patent Number: 5,695,444
Date of Patent: Dec. 9, 1997

[54] MALE ORGAN CONSTRICTOR DEVICE AND METHOD OF USING THE DEVICE

[76] Inventor: John L. Chaney, 156 Broad St., Box 790, Lake Geneva, Wis. 53147

[21] Appl. No.: 504,441

[22] Filed: Jul. 20, 1995

[51] Int. Cl.[6] ....................................................... A61F 5/00
[52] U.S. Cl. ............................................. 600/38; 600/41
[58] Field of Search ....................... 600/38–41; 128/842, 128/45, 885

[56] References Cited

U.S. PATENT DOCUMENTS

| 3,759,253 | 9/1973 | Cray . |  |
|---|---|---|---|
| 4,539,980 | 9/1985 | Chaney . |  |
| 5,224,453 | 7/1993 | Osbon et al. | 600/41 X |
| 5,327,910 | 7/1994 | Flynn | 600/38 X |

OTHER PUBLICATIONS

Webster's II New Riverside University Dictionary, 1994. p. 942. The Riverside Publishing Company.

*Primary Examiner*—Jennifer Bahr
*Assistant Examiner*—Ryan Carter
*Attorney, Agent, or Firm*—Ryan, Maki, Mann & Hohenfeldt

[57] ABSTRACT

An elastic ring for assisting a male to obtain and maintain an erection has two prongs circumferentially spaced apart and extending from the inside diameter of the ring inwardly of the ring opening and has a protuberance formed on the inside of ring substantially diametrically opposite of the prongs. The device is capable of encircling the penis and scrotum so as to apply a compressive force rearwardly of the root of the penis so that the external conspicuous part of the penis and the more concealed root part can become rigidified or erect and involved in the sexual act.

12 Claims, 3 Drawing Sheets

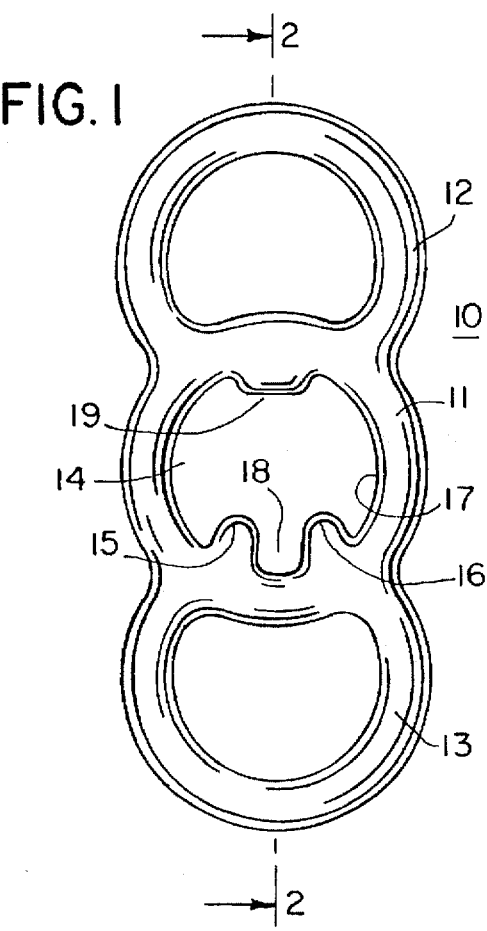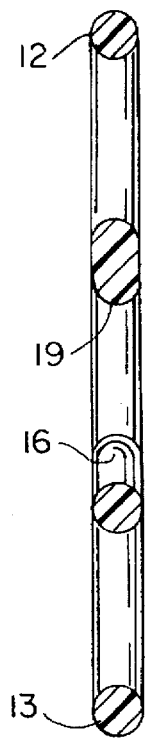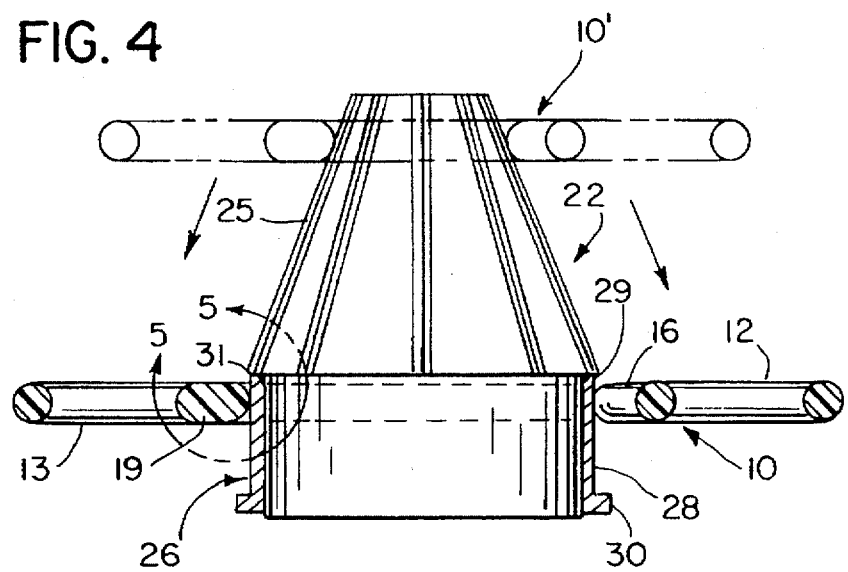

MALE ORGAN CONSTRICTOR DEVICE AND METHOD OF USING THE DEVICE

BACKGROUND OF THE INVENTION

The invention disclosed herein pertains to a device for assisting a male to obtain and maintain an erection of his penis to enable performing sexual intercourse.

It is sufficient to recall, for the purposes of the invention described herein, that the penis is composed of erectile tissue arranged in three longitudinal columns bonded by fibrous tissue. Erectile tissue has a sponge-like structure containing cavernous spaces for being occupied by blood. These spaces are fed by arterioles and capillaries branching from the penile artery and are drained by small flow restricting veins. When the penis is induced to erect, arterioles feeding the corpus cavernosa dilate, the muscle fibers around the cavernosa relax, and the muscle controlling the penis outlets contracts to restrict blood discharged from the cavernosa. The cavernous spaces in the erectile tissue expand as blood is pumped through them at substantially arterial pressure, and the penis becomes hard and erect. Thus, the natural erection process is basically a matter of capturing and holding pressurized blood in the cavernous tissues of the penis.

A device for restricting outflow of venous blood once an erection has been obtained is described in U.S. Pat. No. 4,539,980 in which the inventor is the same as the inventor of the present application. The elastic constrictor ring disclosed in the patent has been used successfully by hundreds, if not thousands, of males to obtain and maintain an erection. The patented elastic constrictor ring is used in two different methods. In one method, the ring is expanded manually and slipped over the penis to the base. The region of the body behind the scrotum is then pressed by the users fingers and drawn forward such as to massage arterial blood into the corpus cavernosa through arteries and arterioles which are arranged primarily in the lower region of the penis along its length. As more blood is massaged into the penis, it expands diametrically and longitudinally. If the constrictor ring chosen is appropriate for the size of the penis, the enlargement of the penis will be counteracted by the elasticity of the ring in which case outflow of venous blood from the penis is restricted. As long as the blood can be trapped in the penis by the ring, the penis remains erect.

Another method for acquiring an erection involves the use of a cylinder to which a pump for generating a vacuum is connected. The constrictor ring is stretched onto the open end portion of the cylinder and the end of the cylinder is pressed against the body with the flaccid penis extending into it. By pressing the cylinder with sufficient force against the body a temporary vacuum tight seal is created. The pump is then operated manually to create a negative pressure inside of the cylinder in which case the higher arterial blood pressure drives blood into the cavernosa, and an erection is thereby acquired. To maintain the erection, the constrictor ring is slipped off the cylinder and onto the base of the penis for preventing outflow of venous blood so the erection will be maintained for the desired utilization.

A problem that is common to methods of obtaining and erection and maintaining it with preexisting constrictor rings is that only that portion of the penis which extends from the base of the penis at the front of the body to the extremity of the glans penis becomes erect, and that muscular root part of the penis which projects out from the scrotum and behind it does not become filled with pressurized blood. Therefore, it does not become rigid. That part of the penis root which is not experiencing hardening which could add to the pleasure and excitement of the female and at the same time give more satisfaction to the male because of the belief that the sex partner is finding the event more pleasurable.

SUMMARY OF THE INVENTION

The primary objective of the present invention is to provide a specially configured restrictor ring that enables obtaining and maintaining an erection without the male resorting to use of the vacuum method or the method involving massaging blood along the scrotum toward the penis as described above. The new constrictor ring is designed for facilitating forcing blood into the penis to cause an erection by voluntary contraction of the pelvic muscle including the pubococcyeous (PC) muscle and/or the levator ani muscle. This muscle is the one that is contracted when one desires to interrupt urination temporarily. Contracting this muscle, repeatedly several times per day on a daily basis exercises the muscle and strengthens it. The PC muscle in both the male and female runs between the pubic bone in front and the coccyx (tail bone) in back and is called the voluntary urinator sphincter muscle. Voluntary tensioning off this muscle can cause an erection. Exercises for toning these muscles are known as Kegel exercises. Cyclically tensing and relaxing the muscle can force blood into the penis and cause an erection which can be attained and maintained using the constrictor ring described hereinafter.

In accordance with the invention, an elastic constrictor ring is provided with a radially inwardly extending protuberance or land that bears on the top of the penis tissue to prevent outflow of venous blood from the penis. The ring is also provided with circumferentially inwardly directed protuberances(called prongs herein) which, of course, also bear upon the penis root tissue behind the scrotum but on the lower surface of the penis. As the ring is stretched, the prongs separate more from each other in the circumferential direction of the ring such that they bear on the lower surface of the penis root on opposite sides of the underlying urethra to keep it open and to allow for free inflow of arterial blood. After the new constrictor ring is installed on the body, the user tenses and relaxes the muscles named above in accordance with the Kegel exercises to force arterial blood into the corpus cavernosa to obtain an erection while the protuberance in the ring which bears on the top of the penis prevents outflow of blood. The ring may have loops formed integrally with its outside rim and diametrically opposite from each other to provide for stretching the ring by hand to enlarge it or remove the ring from the genitals.

A more detailed description of the construction of the ring and the manner in which it is used will now be set forth in reference to the drawings.

DESCRIPTION OF THE DRAWINGS

FIG. 1 is a plan view of an embodiment of the new male organ erection obtaining and maintaining restrictor device;

FIG. 2 is a sectional view taken on a line corresponding with 2—2 in FIG. 1;

FIG. 4 shows a conical member for stretching the ring and having it slide onto the annulus;

DESCRIPTION OF A PREFERRED EMBODIMENT

Figure 5:
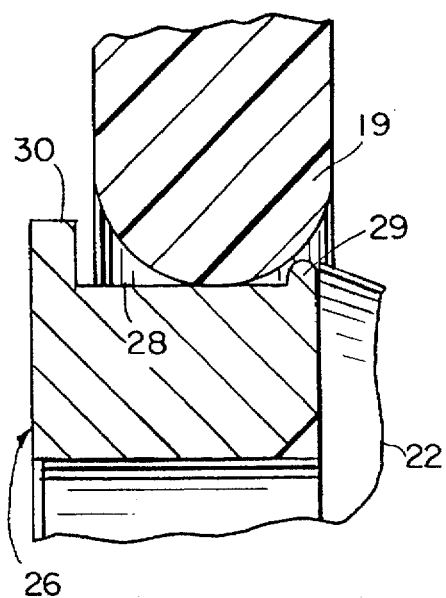
FIG. 5 is a magnified fragmentary sectional view of portions of the ring and annulus that are encompassed within the dashed line circle 5'5 in FIG. 4.

FIG. 1 is a plan view of the new erection obtaining and maintaining device 10 which comprises a central ring 11 and a pair of integral laterally extending elastic loops 12 and 13. The device may be composed of any suitable elastic material such as silicone, natural latex or synthesized natural latex. The new part of the device is the configuration of the central ring 11. Ring 11 surrounds an opening 14 which is illustrated as being circular but it could be oval or some other near-circular configuration. A pair of protuberances 15 and 16, called prongs, project from the inside rim 17 of ring 11 into open space 14. Prongs 15 and 16 have a space 18 between them. The ring in FIG. 1 is presently unstretched so the space 18 is at its narrowest width. Diametrically opposite of the interior of the ring from space 18 there is a land or protuberance 19.

As is evident in FIG. 2, the cross-sectional diameter or thickness of the central ring 11 is the same as the cross-sectional thickness or diameter of the loops 12 and 13. In other words, in this particular embodiment, the two loops 12 and 13 and central ring 11 all have the same thickness. However, it should be understood that loops 12 and 13 are not new parts of the present invention since they have been used before. The new features are all related to the central ring 11 and include prongs 15, 16 and land or protuberance 19. In FIG. 1, the dashed line represents an imaginary plane that bisects ring 11 and the space between prongs 15 and 16. Thus, the prongs are symmetrical to the plane. The outside shape of the device depicted in FIG. 1 is similar to the male organ conditioner shown in U.S. Pat. No. 4,539,980 which issued to the applicant in this application.

By way of example and not limitation, the circumferential length of protuberance 19 is about 0.375 of an inch (9.5 mm). The protuberance projects radially inwardly about 0.125 of an inch (3.175 mm). The cross sectional thickness of the ring is 0.25 of an inch (6.35 mm). The radial length of each prong is about 0.25 of an inch (6.35 mm). The space 18 between prongs 15 and 16 is about 0.25 of an inch (6.35 mm) when the ring is not stretched. The ring size prescribed depends on the penis size of the individual.

Figure 7:
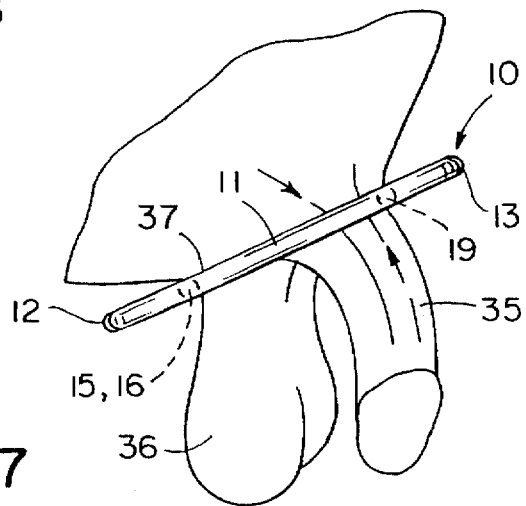
FIG. 7 is similar to FIG. 6 except that the elastic ring has been slid off the rigid annulus and the annulus has been slid over the scrotum and penis to remove the annulus from the body.

The device shown in FIGS. 1 and 2 is designed for being installed in proximity with the male genitals as depicted in FIG. 7 wherein the penis is still in a flaccid state.

Figure 3:
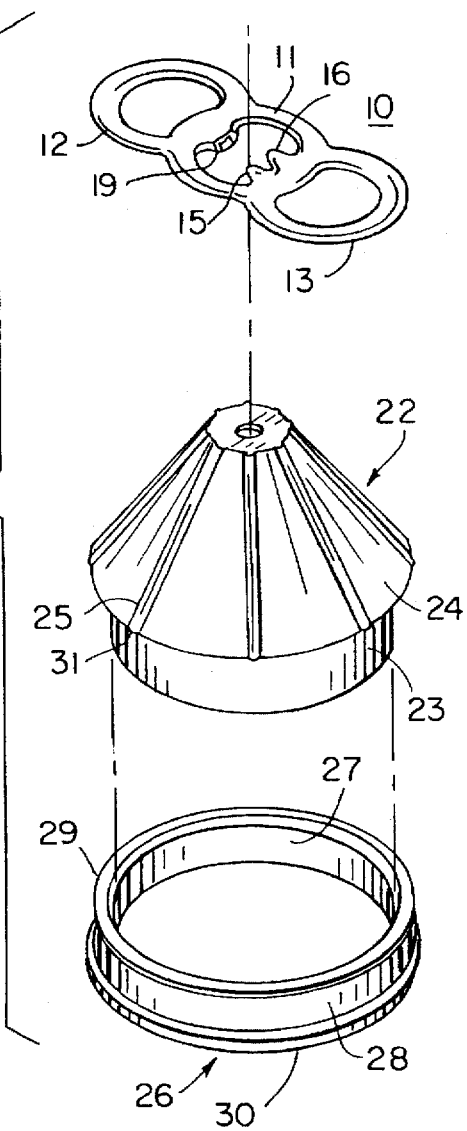
FIG. 3 is a perspective view of the restrictor ring and a conical member which enlarges the ring for it to fit on a rigid annulus that facilitates application of the ring to the root of the penis.

FIGS. 3 and 4 illustrate how the erection obtaining and maintaining device 10 is put in readiness for being deposited on the male genitals. FIG. 3 shows a conical member, generally designated by the numeral 22, which has a circular body 23, to which a conical member 24 is molded unitarily. Conical member 22 is preferably molded of a plastic material. The surface of conical member 22 has some circumferentially spaced apart ribs 25. A ring device transfer annulus, generally designated by the numeral 26, has an inside circular diameter 27 which allows annulus 26 to be telescoped onto cylindrical part 23 of conical member 22. Annulus 26 has an external periphery 28 which has formed on its axially opposite ends circular radially projecting rims 29 and 30. Rims 29 and 30 have outside diameters slightly greater than the outside diameter of cylindrical portion 28 of annulus 26. The radii of the rims are exaggerated relative to the radius of cylindrical part 28 of the annulus as they are drawn in FIG. 3. The reason for this will appear shortly. It should be noted in FIG. 3 that the lower ends 31 of the ribs 25 of conical member 22 will over hang the rim 29 of the annulus by a small amount when the annulus 26 is deposited on cylindrical part 23 of conical member 22.

FIG. 4 shows how elastic device 10 is deposited on annulus 26 while the annulus is telescoped onto the cylindrical part 23 of conical member 22. To put elastic ring device 10 on annulus 26 for facilitating transfer of the ring device 10 to the body as in FIG. 7, the annulus 26 may be set on a hard surface, not shown, with the cylindrical part of the conical member fitted inside of annulus 26 as shown in FIG. 4. The elastic device 10 is placed on the small end of the cone initially wherein it is shown in phantom lines and indicated by the numeral 10'. The intended user then slides the ring device 10, particularly ring 11, down the surface of the cone along ribs 25 whereupon the central ring portion 10 will expand enough to slide from the cone over smaller radius rim 29 onto the cylindrical body 28 of annulus 26. As mentioned earlier in connection with FIG. 3, the lower tips 31 of the ribs 25 overhang the annulus rim 29, so that the elastic ring portion 11 slides off of the cone 22 without significant interference by radially extending rim 29. Rim 29 is intentionally made so its diameter is only slightly in excess of the diameter of annulus 29 body 28. Rim 29 has a large enough size for preventing the device 10 from sliding off cylindrical portion 28 of transfer annulus 26 unless the ring is given a low force push to get it off of the annulus 26 when the elastic ring is being deposited on the genitals of the male. After the device 10 is transferred to annulus 26 from the cone as shown in FIG. 4, the annulus with elastic device 10 on it is slid off the cylindrical part 23 of transfer conical member 22. The annulus with the elastic ring on it can be carried by the male in his pocket to any site where circumstances suggest that it may be desirable to install the device on the genitals.

FIG. 5 is a fragmentary cross-sectional view of the annulus ring 26 taken from the region 5—5 in FIG. 4. The interior periphery of elastic ring 11 is bearing on the periphery 28 of annulus 26. Incidentally, the annulus is crossed hatch to indicate metal, but it will be understood that it could also be composed of a strong resin or plastic such as polycarbonate resin. By way of example and not limitation, the rim 29 preferably extends radially outward from cylindrical body 28 by about 0.015 inch (0.0038 mm). By way of example, the radius of the larger rim 30 may extend radially outward by about 0.010 inch (2.5 mm). Transfer annuluses 26 are made available with various inside and outside diameters so that a male may be provided with one that matches the elastic ring size that has been prescribed as appropriate to his anatomical dimensions. Byway of example and not limitation, the annuluses are made available having an inside diameter ranging from 1.25 inches (31.75 mm) to 3.75 inches (95.25 mm). Transfer cones 22 having an outside diameter of the cylindrical part 23 that mates with the inside diameter of the annulus 26. The annulus must be large enough for the penis and scrotum of the individual to fit through it.

Figure 6:
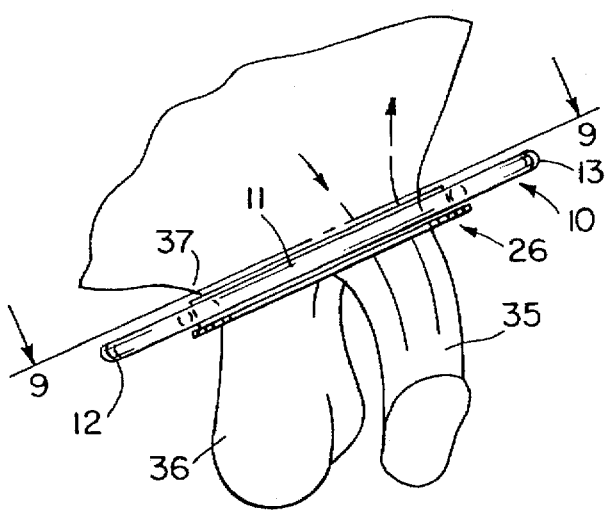
FIG. 6 is a perspective view of the ring located concentrically on the rigid annulus with the annulus having been slid over the top base of the penis and under the root of the penis behind the scrotum.

FIG. 6 shows initial application of the elastic constrictor device 10 to the body in the region of the genitals including the penis 35 and the scrotum. To attain the situation shown in FIG. 6, the scrotum and penis are grasped by one hand of the user while the other hand is available for sliding the annulus 26 over the genitals with the elastic device on the annulus. At this time, the penis 35 is likely to be flaccid as indicated in FIG. 6. The next thing to do is slide the elastic device 10 off the annulus 26 and onto the body. Because the small diameter rim 29 of annulus 29 is small enough to not offer any significant interference against sliding the device 10 off, the elastic restrictor device comes off without contracting so rapidly as to sting the user.

FIG. 7 illustrates the elastic device 10 after it has been deposited on the flaccid penis. At this time, the protuberance 19 of the ring portion 11 is bearing on the top of the penis at its base snugly and not freely if the appropriate ring 11 opening size has been selected. The prongs 15,16 of the elastic ring are pressing against the body immediately behind the scrotum 36 underlying the root of the penis. Prongs 15 and 16 are bearing in a region which is not visible externally of the anatomy where the true root of the penis is located behind the scrotum. The pelvic muscle contraction exercise can now be executed to force blood under pressure into the penis to produce an erection. The root area is marked 37 in FIGS. 6–8. The root of the penis behind the scrotum also becomes rigidified with the penis when an erection has been obtained. There is some blood in the scrotum posterior to the penis root area 37 even after the cavernosa are filled by the pelvic exercise. The erection can be improved and maximized by using the fingers to massage this blood through the restrictor ring into the penis. It is important from the view point of maximizing the pleasure involved in sexual intercourse that the entire length of the penis from its tip to the root 37 be rigid. In prior art constrictor rings which only fit over the penis to its base forward of the scrotum and where the erection has been procured by using the vacuum device or massage technique mentioned earlier, the root of the penis never becomes rigid so only the outer part of the penis 35 participates in penetration. In FIG. 7, the properly sized ring containing device 10 is exerting mild pressure on the top of the penis and rear of the scrotum at the outset of the procedure before an erection is induced.

Figure 8:
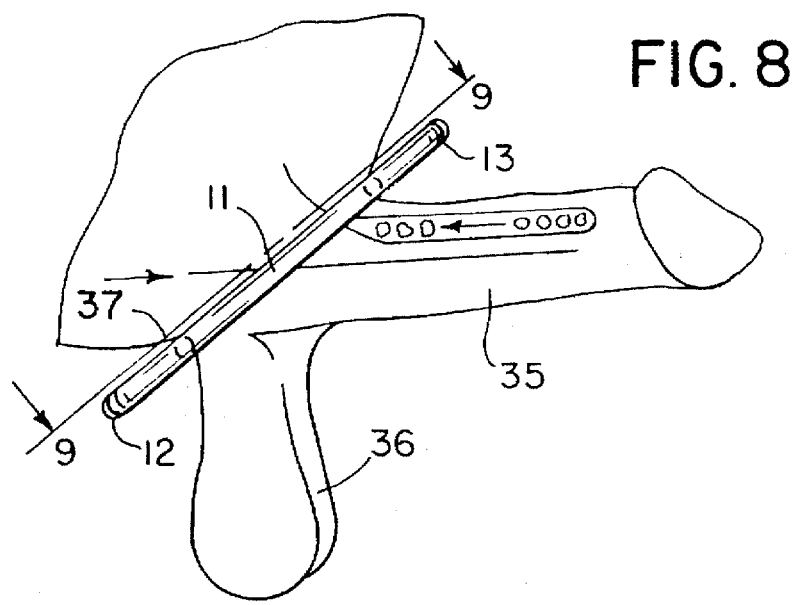
FIG. 8 shows the elastic ring deposited on the body with the penis having become erect.

In FIG. 8, it is assumed that blood has been forced into the penis by cyclically contracting and relieving the levator ani muscle. As soon as the penis begins to enlarge slightly, the elasticity of the central restrictor ring of the device 10 allows it to expand and develop a greater and greater force on the penis, particularly the top of the penis by reason of protuberance 19 bearing on it. Meanwhile, the force applied to the base region 37 of the penis by the elasticity of the device 10 is sufficient to allow arterial blood to be forced into the penis while the force of the protuberance 19 on the top area of the penis prohibits outflow of blood through the veins so that the penis remains rigid. If the erection begins to decline after a period of usage, the user can indulge in repeated cyclic contraction of the levator ani to preserve the erection.

Figure 9:
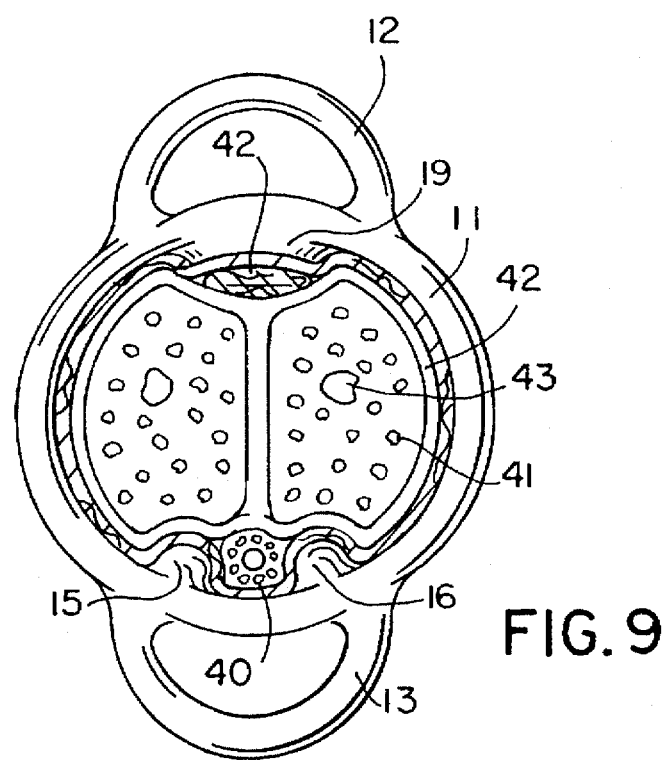
FIG. 9 is a vertical sectional view of the penis, with the ring installed, taken on a line corresponding with 9—9 in FIG. 6.

FIG. 9 is an approximately realistic cross-section of the anatomy taken at the plane corresponding to 9—9 in FIG. 8. This is symbolic of an erection having been obtained. Here one may see that the prongs 15 and 16 are expanded or separated from each other by an amount that is greater than the separation 18 in FIG. 1 so a space develops for accommodating the urethra 40 between the prongs. Meanwhile the two prongs 15 and 16 exert pressure in the arterial blood infeed region of the penis. Thus, the lower part of the ring 11 proximate to prongs 15 and 16 constitutes a one way check valve due to the elasticity of the ring. The corpora cavernosum 41 are filled with blood which rigidifies the penis. Outflow of blood from the penis through the veins 42 is restricted by the pressure applied by the protuberance 19 on the top part of the penis. The whole of the structure of the corpora cavernosa contained within the fibrous sheath 42 of the penis consists of a sponge-like tissue of small spaces freely communicating with each other and filled with venous blood. The deep arteries that supply the corpora cavernosum with blood are marked 43 in FIG. 9.

In summary, an elastic ring member 10 has been described and a method of using it has also been described for use in obtaining and maintaining an erection, not only of the conspicuous outer part of the rigid penis, but also of the sexually useful root part of the penis where the ring is designed for encircling the penis body and the region behind the penis root as well. This increases the effective rigid length of the penis as compared with elastic rings that are applied only to the base of the penis forward of the root without applying pressure to the root behind the scrotum.

Although the structure of a new sexual aid device and the method of using it have been described in detail, such description is intended to be illustrative rather than limiting, for the invention may be variously embodied and is to be limited only by interpretation of the claims which follow.

I claim:

1. A male sexual aid device comprising:

a ring, composed solely of elastic material which is self restoring to its original shape when it is released after having been deformed, having an inside surface defining an opening, a first protuberance projecting a shod distance into said opening from said inside surface of said ring, and two protuberances that are spaced apart from each other, and project into said opening from said inside surface of said ring in a direction generally opposite of the direction in which said first protuberance projects.

2. A device according to claim 1 wherein said spaced apart protuberances are positioned symmetrically to a line that bisects said opening, said first protuberance and said space between said two protuberances.

3. A device according to claim 1 wherein said ring has a circular periphery and said opening is circular other than where said first protuberance and said two protuberances are positioned and the difference between the radius of said periphery and the radius of said opening is about 0.25 inches (6.35 mm).

4. A device according to claim 1 wherein the length of said two protuberances extending into said opening are each about 0.25 of an inch (6.35 mm).

5. A device according to claim 1 wherein said ring is composed solely of an elastic material selected from the class of rubber, silicone, natural latex and synthetic latex.

6. A device according to claim 1 including a pair of loops composed of said elastic material, one of said loops is joined integrally with said ring radially outwardly of and symmetrically with said first protuberance and the other of said loops is joined with said ring radially outwardly of and symmetrically with the space between said two protuberances.

7. A device according to claim 1 wherein said first protuberance projects from said inside surface of said ring by about 0.125 of an inch (3.175 mm).

8. A male sexual aid device comprising:

a ring, composed solely of elastic material, having an inside surface defining an opening, a first protuberance projecting a short distance into said opening from said inside surface of said ring, and two protuberances that are spaced apart from each other and project into said opening from said inside surface of said ring in a direction generally opposite of the direction in which said first protuberance projects, the first protuberance having a length extending along said inside surface of the ring of about 0.375 inches (9.5 mm).

9. A device according to claim 8 wherein said first protuberance projects from said inside surface of said ring by about 0.125 of an inch (3.175 mm).

10. A device according to claim 8 wherein said ring has a circular periphery and said opening is circular other than where said first protuberance and said two protuberances are positioned and the difference between the radius of said periphery and the radius of said opening is about 0.25 inches (6.35 mm).

11. A device according to claim 8 wherein the length Of said two protuberances extending into said opening are each about 0.25 of an inch (6.35 mm).

12. A method for a male to prepare for obtaining and maintaining an erection comprising the steps of:

providing an elastic ring that has an inside surface defining an opening with a first protuberance projecting from said inside surface inwardly of the opening and a pair of spaced apart protuberances projecting from said inside surface inwardly of said opening oppositely of said first protuberance, stretching said ring onto a rigid annulus, manipulating the penis and scrotum of said male through said annulus to position said first protuberance of said ring in alignment with the top of the penis at the base of the penis and to position said pair of protuberances in stretched apart condition subjacent the root of the penis behind the scrotum, then sliding said elastic ring off said annulus to provide for having said first protuberance press on the top of the penis at said base of the penis and for having said protuberance in said pair press on the root of the penis on opposite sides of where the urethra passes through the root.

* * * * *

UNITED STATES PATENT AND TRADEMARK OFFICE
CERTIFICATE OF CORRECTION

PATENT NO. : 5,695,444
DATED : December 9, 1997
INVENTOR(S) : John L. Chaney

It is certified that error appears in the above-identified patent and that said Letters Patent is hereby corrected as shown below:

Column 6, Line 32    Delete "shod" and substitute --- short ---

Column 7, Line 17    Delete "Of" and substitute --- of ---

Signed and Sealed this

Third Day of March, 1998

Attest:

BRUCE LEHMAN

Attesting Officer         Commissioner of Patents and Trademarks